United States Patent
Neben et al.

(10) Patent No.: US 11,617,565 B2
(45) Date of Patent: Apr. 4, 2023

(54) METHODS AND APPARATUSES FOR COLLECTION OF ULTRASOUND DATA ALONG DIFFERENT ELEVATIONAL STEERING ANGLES

(71) Applicant: BFLY Operations, Inc., Guilford, CT (US)

(72) Inventors: Abraham Neben, Guilford, CT (US); Nevada J. Sanchez, Guilford, CT (US); Karl Thiele, St. Petersburg, FL (US)

(73) Assignee: BFLY OPERATIONS, INC., Burlington, MA (US)

( * ) Notice: Subject to any disclaimer, the term of this patent is extended or adjusted under 35 U.S.C. 154(b) by 22 days.

(21) Appl. No.: 16/900,117

(22) Filed: Jun. 12, 2020

(65) Prior Publication Data

US 2020/0390419 A1 Dec. 17, 2020

Related U.S. Application Data

(60) Provisional application No. 62/862,008, filed on Jun. 14, 2019.

(51) Int. Cl.
*A61B 8/00* (2006.01)
*A61B 8/08* (2006.01)
*A61N 7/00* (2006.01)
*A61B 8/12* (2006.01)

(52) U.S. Cl.
CPC .............. *A61B 8/4494* (2013.01); *A61B 8/08* (2013.01); *A61B 8/0883* (2013.01); *A61B 8/12* (2013.01); *A61B 8/4236* (2013.01); *A61B 8/4427* (2013.01); *A61N 7/00* (2013.01)

(58) Field of Classification Search
CPC .... A61B 8/4494; A61B 8/4488; A61B 8/5253
See application file for complete search history.

(56) References Cited

U.S. PATENT DOCUMENTS 5,148,810 A * 9/1992 Maslak ............... G01S 15/8927
600/447
5,301,168 A 4/1994 Miller
5,462,057 A * 10/1995 Hunt .................... G01S 7/52046
600/447

(Continued)

FOREIGN PATENT DOCUMENTS

WO WO 2017/222964 A1 12/2017

OTHER PUBLICATIONS

International Search Report and Written Opinion dated Sep. 3, 2020 in connection with International Application No. PCT/US2020/037483.

(Continued)

*Primary Examiner* — Joel Lamprecht
*Assistant Examiner* — Nyrobi Celestine
(74) *Attorney, Agent, or Firm* — Osha Bergman Watanabe & Burton LLP

(57) ABSTRACT

Ultrasound devices and methods are described for collecting ultrasound data. An ultrasound device may include an ultrasound transducer array. The ultrasound device may collect ultrasound data along multiple elevational steering angles with respective apertures of different sizes. The ultrasound data may be used to perform a measurement or generate a visualization.

20 Claims, 10 Drawing Sheets

(56) References Cited

U.S. PATENT DOCUMENTS

| | | | |
|---|---|---|---|
| 5,490,512 A * | 2/1996 | Kwon | G01S 15/8925 600/447 |
| 5,671,746 A | 9/1997 | Dreschel et al. | |
| 5,677,491 A * | 10/1997 | Ishrak | A61B 8/4483 310/335 |
| 5,911,221 A * | 6/1999 | Teo | G01S 15/8925 600/447 |
| 5,931,785 A * | 8/1999 | Mason | B06B 1/0629 600/459 |
| 6,464,638 B1 * | 10/2002 | Adams | G01S 15/8995 600/443 |
| 8,852,103 B2 | 10/2014 | Rothberg et al. | |
| 9,084,576 B2 * | 7/2015 | Guracar | A61B 8/06 |
| 9,521,991 B2 | 12/2016 | Rothberg et al. | |
| 9,592,030 B2 | 3/2017 | Rothberg et al. | |
| 9,986,969 B2 | 6/2018 | Call et al. | |
| 10,702,242 B2 | 7/2020 | de Jonge et al. | |
| 10,709,415 B2 | 7/2020 | Neben et al. | |
| 11,041,945 B2 * | 6/2021 | Lee | G01S 15/8995 |
| 2004/0054285 A1 * | 3/2004 | Freiburger | G01S 7/52046 600/447 |
| 2009/0005684 A1 | 1/2009 | Kristofferson et al. | |
| 2011/0055447 A1 | 3/2011 | Costa | |
| 2014/0031673 A1 * | 1/2014 | Amemiya | A61B 8/0841 600/459 |
| 2017/0360397 A1 | 12/2017 | Rothberg et al. | |
| 2017/0360399 A1 | 12/2017 | Rothberg et al. | |
| 2017/0360401 A1 | 12/2017 | Rothberg et al. | |
| 2017/0360402 A1 | 12/2017 | de Jonge et al. | |
| 2017/0360403 A1 | 12/2017 | Rothberg et al. | |
| 2017/0360404 A1 | 12/2017 | Gafner et al. | |
| 2017/0360411 A1 | 12/2017 | Rothberg et al. | |
| 2017/0360412 A1 | 12/2017 | Rothberg et al. | |
| 2018/0008233 A1 * | 1/2018 | Pelissier | G01S 15/892 |
| 2018/0085096 A1 * | 3/2018 | Brandl | A61B 8/469 |
| 2019/0142388 A1 | 5/2019 | Gonyeau et al. | |
| 2019/0150887 A1 * | 5/2019 | Nikolov | G01S 7/52049 |
| 2019/0307428 A1 | 10/2019 | Silberman et al. | |
| 2020/0046314 A1 | 2/2020 | Neben et al. | |
| 2020/0129151 A1 | 4/2020 | Neben et al. | |
| 2020/0155113 A1 | 5/2020 | Neben et al. | |

OTHER PUBLICATIONS

International Preliminary Report on Patentability for International Application No. PCT/US2020/037483, dated Dec. 23, 2021.

* cited by examiner

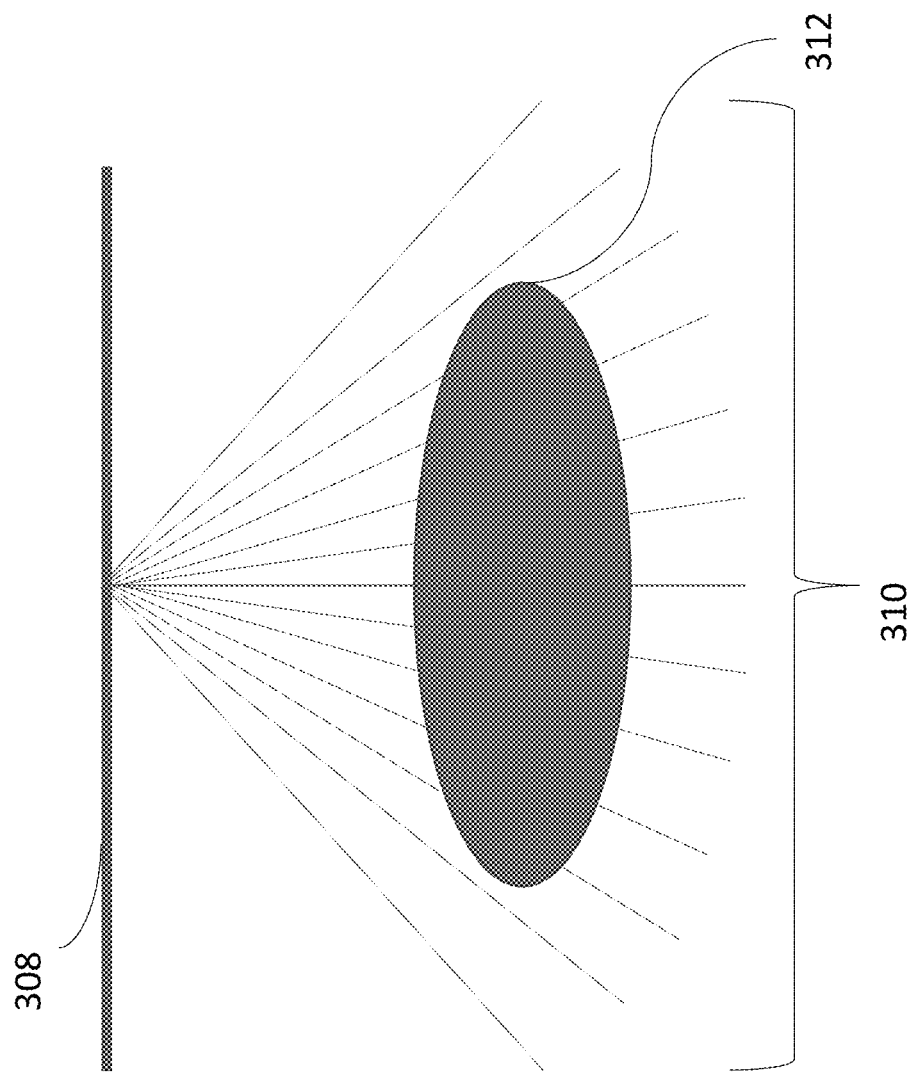

METHODS AND APPARATUSES FOR COLLECTION OF ULTRASOUND DATA ALONG DIFFERENT ELEVATIONAL STEERING ANGLES

CROSS-REFERENCE TO RELATED APPLICATIONS

This application claims the benefit under 35 U.S.C. § 119(e) of U.S. Patent Application Ser. No. 62/862,008, filed Jun. 14, 2019 under, and entitled "METHODS AND APPARATUSES FOR COLLECTION OF ULTRASOUND DATA ALONG DIFFERENT ELEVATIONAL STEERING ANGLES," which is hereby incorporated by reference herein in its entirety.

FIELD

Generally, the aspects of the technology described herein relate to collection of ultrasound data. Some aspects relate to collecting ultrasound data along different elevational steering angles.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the present application, an ultrasound device is provided, the ultrasound device comprising an ultrasound transducer array. The ultrasound device is configured to: collect first ultrasound data along a first elevational steering angle with a first aperture of the ultrasound transducer array; and collect second ultrasound data along a second elevational steering angle with a second aperture of the ultrasound transducer array. The first aperture is a different size than the second aperture.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 3A illustrates a schematic of an ultrasound imaging sweep, in accordance with certain embodiments described herein;

DETAILED DESCRIPTION

Figure 1:
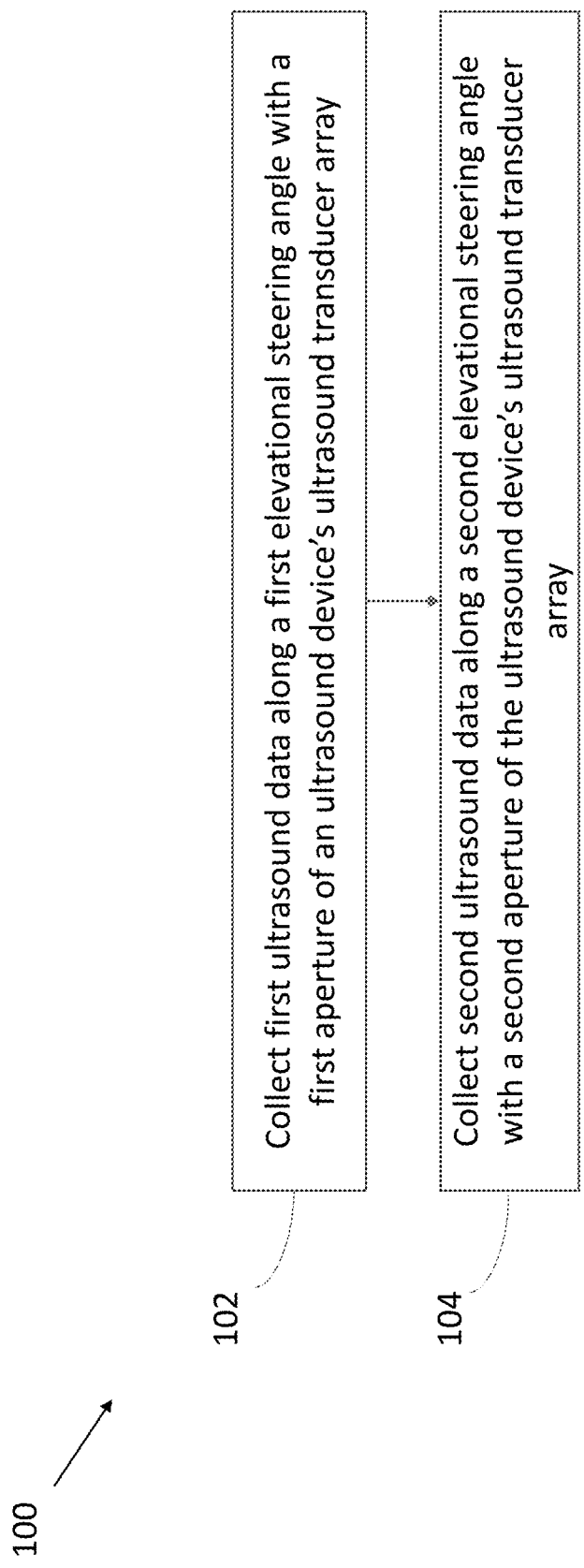
FIG. 1 illustrates a process for collection of ultrasound data of an anatomical structure, in accordance with certain embodiments described herein.

Ultrasound imaging sweeps may be useful for certain applications. For example, an ultrasound imaging sweep may be used for collecting three-dimensional data for measuring the volume of an anatomical structure and/or for generating a three-dimensional visualization of an anatomical structure. An ultrasound imaging sweep may include collecting ultrasound data sets, one after another, with successive iterations of transmitting and receiving ultrasound waves. Each set of ultrasound data collected from the successive iterations of transmitting and receiving ultrasound waves may be focused at different steering angles using beamforming. The different steering angles may vary in azimuth and elevation, defined as the angles along the long and short axis of the ultrasound transducer array, respectively. The beamforming process may include applying different delays to the transmitted and received ultrasound waves/data from different portions of the ultrasound transducer array (e.g., different delays for different elevational rows, where a row refer to a sequence of elements at the same position on the short axis of the ultrasound transducer array). The delays may be applied by an ultrasound device that transmits and receives ultrasound waves and/or by a processing device that processes the resulting data.

The signal-to-noise ratio of ultrasound data collected at a zero elevational steering angle (i.e., a steering angle that is normal to the elevational dimension of the ultrasound transducer array) may be greater than that of ultrasound data collected at non-zero elevational steering angles. This may be due to the fixed beam pattern of each individual element which results in more transmit/receive power at zero elevation than at non-zero elevations. This may also be due to the increased effect of glancing reflections at large elevations. The greater the divergence from the zero elevational steering angle, the smaller the received/transmitted signal may be, relative to a constant electronic noise floor. This reduced signal-to-noise ratio may be especially evident when ultrasound data is digitally beamformed (i.e., after ultrasound data has been converted to digital) along the elevational dimension of the ultrasound transducer array. The inventors have recognized that signal-to-noise ratio at more extreme elevational steering angles may be increased by transmitting ultrasound waves from/receiving ultrasound waves using a larger elevational aperture of the ultrasound transducer array (i.e., by using more elevational rows). Thus, aspects of the disclosure described herein relate to varying the elevational aperture during an elevational sweep as a function of elevational steering angle. In particular, the elevational aperture may be increased with more extreme elevational steering angles. In some embodiments, the number of elevational rows used at different iterations of transmitting and receiving ultrasound waves during the sweep may vary between approximately 8-64.

Certain aspects of the disclosure described herein, such as elevational sweeps, may be performed by an ultrasound device that includes ultrasound transducers (e.g., capacitive micromachined ultrasound transducers (CMUTs)) and circuitry integrated on one or more dies (e.g., one or more semiconductor dies). The ultrasound transducers may be arranged in a two-dimensional array on a die. The circuitry may include, for example, ultrasound circuitry for transmitting and receiving ultrasound waves. The ultrasound transducers and the ultrasound circuitry or a portion thereof may be integrated on the same die. The one or more dies on which the ultrasound transducers and circuitry are integrated may be incorporated in a portable form factor. For example, the ultrasound device may be in a form factor of a handheld probe, in a form factor of a wearable patch, and/or in a form factor of an ingestible pill, and the ultrasound transducers and circuitry may be contained in the handheld probe, wearable patch, or ingestible pill.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates a process 100 for collection of ultrasound data of an anatomical structure, in accordance with certain embodiments described herein. The process 100 is performed by an ultrasound device. The ultrasound device includes an ultrasound transducer array and ultrasound circuitry. The ultrasound circuitry may include, for example, transmit and/or receive circuitry, all of which or a portion of which may be integrated on the same die as the ultrasound transducer array. The ultrasound device may be in operative communication with a processing device. The processing device may be, for example, a mobile phone, tablet, or laptop in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

In act 102, the ultrasound device collects first ultrasound data along a first elevational steering angle with a first aperture of the ultrasound device's ultrasound transducer array. Collecting the first ultrasound data may include transmitting and/or receiving ultrasound waves with the ultrasound transducer array, and the ultrasound circuitry may apply delays to ultrasound waves prior to their transmission and/or subsequent to their reception. The first aperture may be, for example, a first number of elevational rows of the ultrasound transducer array. In some embodiments, the processing device may configure the ultrasound device to collect the first ultrasound data, for example, by transmitting control signals to the ultrasound device over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 100 proceeds from act 102 to act 104.

In act 104, the ultrasound device collects second ultrasound data along a second elevational steering angle with a second aperture of the ultrasound device's ultrasound transducer array. Collecting the second ultrasound data may include transmitting and/or receiving ultrasound waves with the ultrasound transducer array, and the ultrasound circuitry may apply delays to ultrasound waves prior to their transmission and/or subsequent to their reception. The second elevational steering angle may be different than the first elevational steering angle. The second aperture may be a different size than the first aperture. The second aperture may be, for example, a second number of elevational rows of the ultrasound transducer array, and the second number of elevational rows may be different than the first number of elevational rows of the first aperture. In some embodiments, when the first elevational steering angle is farther from normal to the elevational dimension of the ultrasound transducer array than the second elevational steering angle, the first aperture may be larger than the second aperture, and vice versa. Thus, in some embodiments, when the first elevational steering angle is farther from normal to the elevational dimension of the ultrasound transducer array than the second elevational steering angle, the first aperture may include more elevational rows than the second aperture, and vice versa. In some embodiments, the processing device may configure the ultrasound device to collect the second ultrasound data, for example, by transmitting control signals to the ultrasound device over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the ultrasound device may digitally beamform (e.g., using the ultrasound circuitry) the first and second ultrasound data along the elevational dimension of the ultrasound transducer array. In some embodiments, the ultrasound device may transmit the first and second ultrasound data and/or data generated based on the first and second ultrasound data (e.g., scan lines and/or ultrasound images generated based on raw acoustical data) to the processing device over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

In some embodiments, the ultrasound device may collect the first ultrasound data and second ultrasound data as part of a single scan, such as a single ultrasound imaging sweep. In particular, the ultrasound imaging sweep may be an elevational sweep. The single scan may collect three-dimensional ultrasound data of an anatomical structure such as a bladder. It should be appreciated that as part of the single scan (e.g., the ultrasound imaging sweep), the ultrasound device may additionally (i.e., in addition to acts 102 and 104) collect third ultrasound data along a third elevational steering angle with a third aperture of the ultrasound device's ultrasound transducer array, fourth ultrasound data along a fourth elevational steering angle with a fourth aperture of the ultrasound device's ultrasound transducer array, etc. In some embodiments, the number of elevational rows used for the aperture at different iterations of transmitting and receiving ultrasound waves during the sweep may vary between approximately 8-64. In some embodiments, the ultrasound device may collect between approximately 30-50 sets of ultrasound data at different elevational steering angles during the sweep, and may use different apertures for collecting certain of these sets of ultrasound data.

Figure 2:
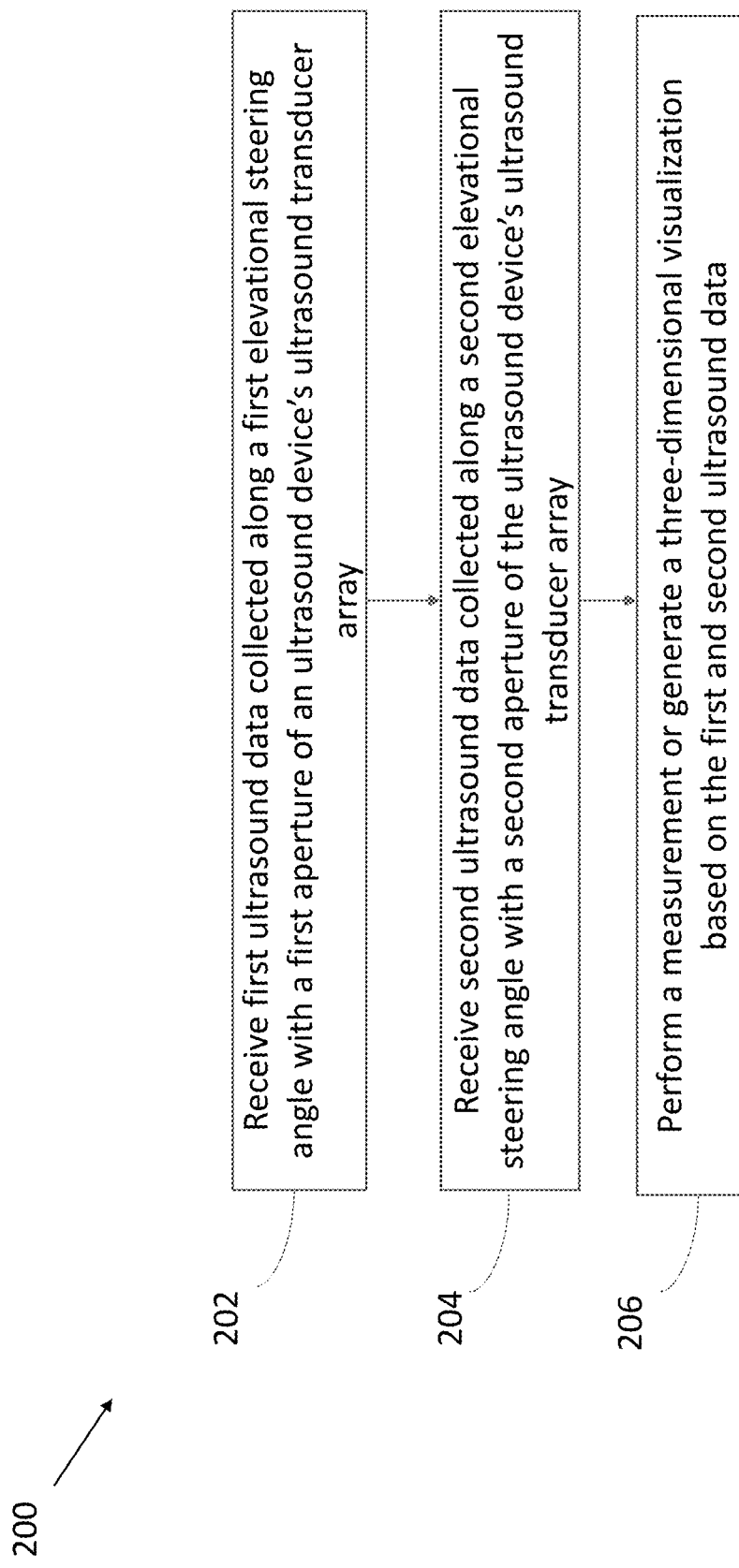
FIG. 2 illustrates a process for collection of ultrasound data of an anatomical structure, in accordance with certain embodiments described herein.

FIG. 2 illustrates a process 200 for collection of ultrasound data of an anatomical structure, in accordance with certain embodiments described herein. The process 200 is performed by a processing device in operative communication with an ultrasound device. The processing device may be, for example, a mobile phone, tablet, or laptop in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

In act 202, the processing device receives, from the ultrasound device, first ultrasound data that was collected along a first elevational steering angle with a first aperture of the ultrasound device's ultrasound transducer array. Collecting the first ultrasound data may include the processing device configuring the ultrasound device to transmit and/or receive ultrasound waves, and the processing device and/or the ultrasound device may apply delays to ultrasound waves/data prior to transmission and/or subsequent to their reception. The first aperture may be, for example, a first number of elevational rows of the ultrasound transducer array. Further description of collecting the first ultrasound data may be found with reference to act 102. The processing device may receive the first ultrasound data from the ultrasound device over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 200 proceeds from act 202 to act 204.

In act 204, the processing device receives, from the ultrasound device, second ultrasound data along a second elevational steering angle with a second aperture of an ultrasound device's ultrasound transducer array. Collecting the second ultrasound data may include the processing device configuring the ultrasound device (e.g., configuring ultrasound circuitry in the ultrasound device) to transmit and/or receive ultrasound waves, and the processing device and/or the ultrasound device may apply delays to ultrasound waves/data prior to transmission and/or subsequent to their reception. The second elevational steering angle may be different than the first elevational steering angle. The second aperture may be a different size than the first aperture. The second aperture may be, for example, a second number of elevational rows of the ultrasound transducer array, and the second number of elevational rows may be different than the first number of elevational rows of the first aperture. In some embodiments, when the first elevational steering angle is farther from normal to the elevational dimension of the ultrasound transducer array than the second elevational steering angle, the first aperture may be larger than the second aperture, and vice versa. Thus, in some embodiments, when the first elevational steering angle is farther from normal to the elevational dimension of the ultrasound transducer array than the second elevational steering angle, the first aperture may include more elevational rows than the second aperture, and vice versa. Further description of collecting the second ultrasound data may be found with reference to act 104. In some embodiments, the first and second ultrasound data may be digitally beamformed along the elevational dimension of the ultrasound transducer array. The processing device may receive the second ultrasound data from the ultrasound device over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The process 200 proceeds from act 204 to act 206.

In act 206, the processing device performs a measurement or generates a three-dimensional visualization based on the first and second ultrasound data. For example, the first ultrasound data and second ultrasound data may be collected as part of a single scan, such as a single ultrasound imaging sweep. In particular, the ultrasound imaging sweep may be an elevational sweep. The single scan may collect three-dimensional ultrasound data of an anatomical structure such as a bladder. Based on this three-dimensional ultrasound data, the volume of the anatomical structure may be measured and/or a three-dimensional visualization of the anatomical structure may be generated. In some embodiments, act 106 may be absent.

It should be appreciated that as part of the single scan (e.g., the ultrasound imaging sweep), the processing device may additionally (i.e., in addition to acts 202 and 204) receive, from the ultrasound device, third ultrasound data collected along a third elevational steering angle with a third aperture of the ultrasound device's ultrasound transducer array, receive fourth ultrasound data collected along a fourth elevational steering angle with a fourth aperture of the ultrasound device's ultrasound transducer array, etc. In some embodiments, the number of elevational rows used for the aperture at different iterations of transmitting and receiving ultrasound waves during the sweep may vary between approximately 8-64. In some embodiments, the processing device may receive between approximately 30-50 sets of ultrasound data collected at different elevational steering angles during the sweep, and the ultrasound device may use different apertures for collecting certain of these sets of ultrasound data. All this ultrasound data may be used to perform the measurement and/or to generate the three-dimensional visualization at act 206.

FIG. 3A illustrates a schematic of an ultrasound imaging sweep, in accordance with certain embodiments described herein. The ultrasound imaging sweep may be collected as described with reference to the processes 100 and 200. FIG. 3A illustrates a skin line 308 of a subject, elevational steering angles 310 (which may include the first and second elevational steering angles described above with reference to the processes 100 and 200), and an anatomical structure 312. The elevational steering angles 310 illustrate different focusing directions during the sweep. The elevational steering angles 310 are varied with respect to an axis that is parallel to the skin line 308 of the subject. Based on ultrasound data collected during the sweep (e.g., along each of the elevational steering angles 310), a measurement of the anatomical structure 312 may be performed or a three-dimensional visualization of the anatomical structure 312 may be generated. In some embodiments, there may be between approximately 30-50 different elevational steering angles 310 used and 30-50 different ultrasound images collected and used for performing the measurement or generating the three-dimensional visualization. In some embodiments, the number of elevational steering angles 310 may be greater for deeper anatomical structures 312 and fewer for shallower anatomical structures. This is because deeper anatomical structures 312 may be bigger than shallower anatomical structures 312, and using more elevational steering angles 310 may help to image the deeper anatomical structures with a similar resolution as shallower anatomical structures 312.

Figure 3B:
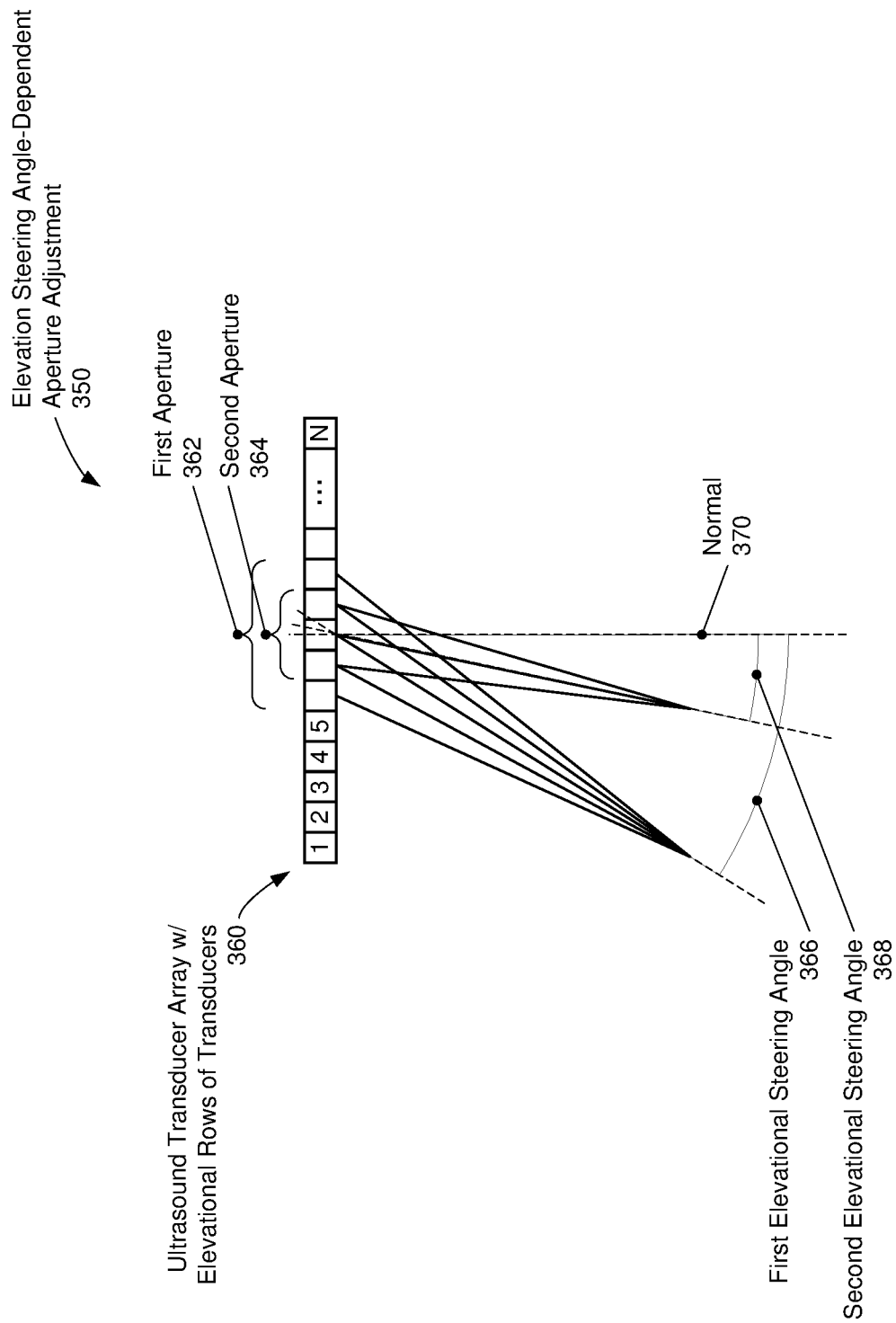
FIG. 3B illustrates an elevation steering angle-dependent aperture adjustment, in accordance with certain embodiments described herein.

FIG. 3B illustrates an elevation steering angle-dependent aperture adjustment 350, in accordance with certain embodiments described herein. An ultrasound transducer array 360 includes N (1, 2, 3, . . . , N) elevational rows of transducers. As shown in FIG. 3B and discussed in reference to the flowcharts, first ultrasound data are collected along a first elevational steering angle 366, with the steering angle being measured from a normal direction 370 that is normal to the elevational dimension of the ultrasound transducer. Further, second ultrasound data are collected along a second elevational steering angle 368, also measured from the normal direction 370. As FIG. 3B illustrates, the first elevational steering angle 366 deviates more from the normal 370 than the second elevational steering angle 368. FIG. 3B also illustrates that the first aperture 362 is a different size than the second aperture 364. Specifically, the first aperture 362 comprises more elevational rows of transducers than the second aperture 364. While the example of FIG. 3B shows the first aperture 362 comprising five elevational rows of transducers, and the second aperture 364 comprising three elevational rows of transducers, the first aperture and the second aperture may have any number of elevational rows of transducers, as long as the first aperture has more rows than the second aperture.

While the above description has used the bladder as an exemplary anatomical structure, the methods and apparatuses described herein may also be applied to collecting ultrasound images for other applications and anatomical structures. For example, the methods and apparatuses may be used for cardiac applications, such as measuring the volume and/or generating three-dimensional visualizations of the left ventricle.

Figure 4:
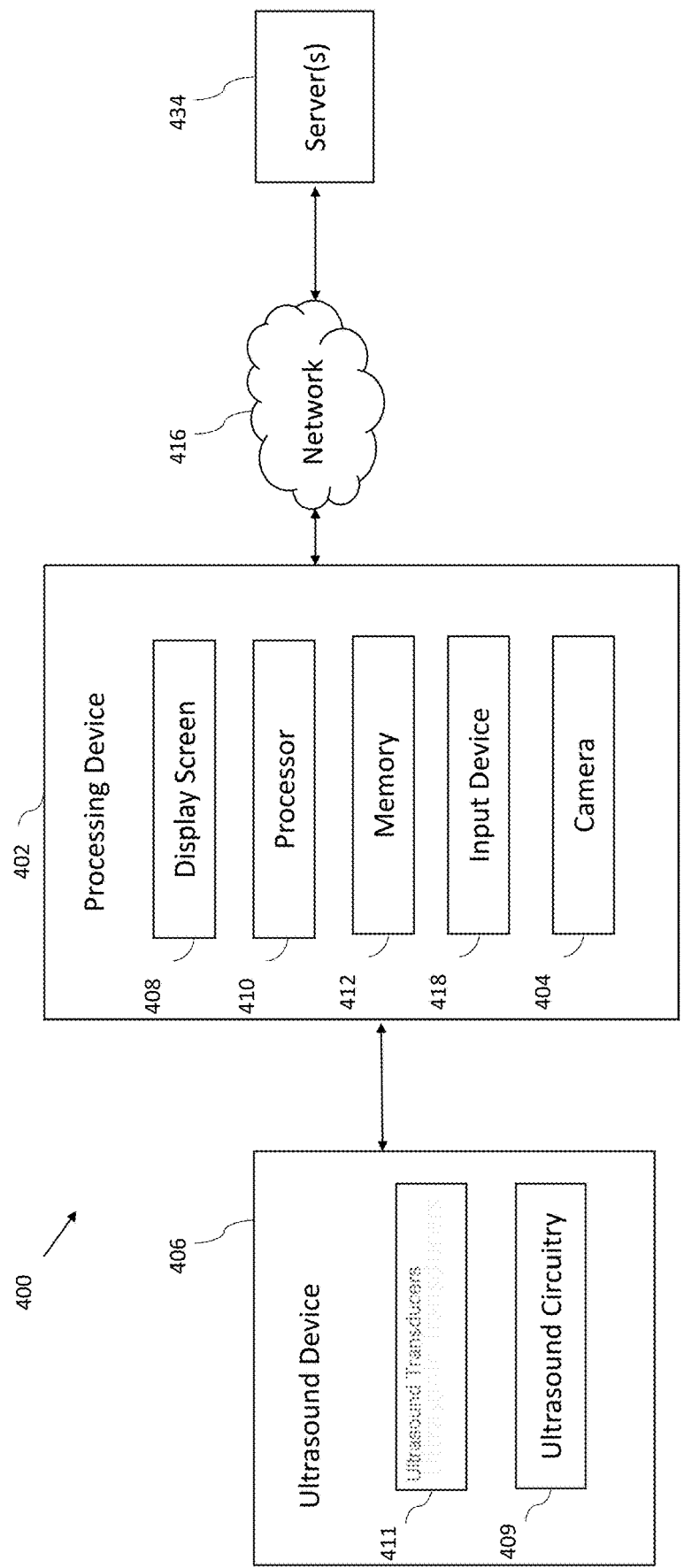
FIG. 4 illustrates a schematic block diagram of an example ultrasound system, in accordance with certain embodiments described herein.

FIG. 4 illustrates a schematic block diagram of an example ultrasound system 400, in accordance with certain embodiments described herein. The ultrasound system 400 includes an ultrasound device 406, a processing device 402, a network 416, and one or more servers 434. The ultrasound device 406 may be any of the ultrasound devices described herein (e.g., the ultrasound device that performs the process 100, the ultrasound device 500, the handheld ultrasound probe 700, the wearable ultrasound patch 800, and/or the ingestible ultrasound pill 900). The processing device 402 may be any of the processing devices described herein (e.g., the processing device that performs the process 200).

The ultrasound device 406 includes ultrasound transducers 411 and ultrasound circuitry 409. The processing device 402 includes a camera 404, a display screen 408, a processor 410, a memory 412, and an input device 418. The processing device 402 is in wired (e.g., through a lightning connector or a mini-USB connector) and/or wireless communication (e.g., using BLUETOOTH, ZIGBEE, and/or WiFi wireless protocols) with the ultrasound device 406. The processing device 402 is in wireless communication with the one or more servers 434 over the network 416. However, the wireless communication with the processing device 434 is optional.

The ultrasound device 406 may be configured to generate ultrasound data that may be employed to generate an ultrasound image. The ultrasound device 406 may be constructed in any of a variety of ways. The ultrasound transducers 411 may be monolithically integrated onto a single semiconductor die. The ultrasound transducers 411 may include, for example, one or more capacitive micromachined ultrasound transducers (CMUTs), one or more CMOS (complementary metal-oxide-semiconductor) ultrasound transducers (CUTs), one or more piezoelectric micromachined ultrasound transducers (PMUTs), and/or one or more other suitable ultrasound transducer cells. In some embodiments, the ultrasound transducers 411 may be arranged in a two-dimensional array. In some embodiments, the ultrasound transducers 411 may be integrated on the same die as certain other electronic components in the ultrasound circuitry 409 (e.g., transmit circuitry, receive circuitry, control circuitry, power management circuitry, and/or processing circuitry) to form a monolithic ultrasound device. In some embodiments, the ultrasound transducers 411 and certain components of the ultrasound circuitry 409 may be integrated on one die and other components of the ultrasound circuitry 409 may be integrated on another die. In some embodiments, the ultrasound circuitry 409 may include transmit circuitry that transmits a signal to a transmit beamformer which in turn drives the ultrasound transducers 411 elements within a transducer array to emit pulsed ultrasonic signals into a structure, such as a patient. The pulsed ultrasonic signals may be back-scattered from structures in the body, such as blood cells or muscular tissue, to produce echoes that return to the ultrasound transducers 411. These echoes may then be converted into electrical signals by the ultrasound transducers 411 and the electrical signals are received by receive circuitry in the ultrasound circuitry 409. The electrical signals representing the received echoes are sent to a receive beamformer in the ultrasound circuitry 409 that outputs ultrasound data. The ultrasound device 406 may use the ultrasound transducers 411 to transmit and/or receive ultrasound waves and may use the ultrasound circuitry 409 to apply delays prior to transmission and/or subsequent to reception of the ultrasound waves in order to collect ultrasound data along different elevational steering angles with different apertures, as described with reference to the process 100. The ultrasound device 406 may transmit ultrasound data and/or ultrasound images to the processing device 402 over a wired (e.g., through a lightning connector or a mini-USB connector) and/or wireless (e.g., using BLUETOOTH, ZIGBEE, and/or WiFi wireless protocols) communication link.

Referring now to the processing device 402, the processor 410 may include specially-programmed and/or special-purpose hardware such as an application-specific integrated circuit (ASIC). For example, the processor 410 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The processing device 402 may be configured to process the ultrasound data received from the ultrasound device 406 to generate ultrasound images for display on the display screen 408. The processing may be performed by, for example, the processor 410. The processor 410 may also be adapted to control the acquisition of ultrasound data with the ultrasound device 406. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 402 may be configured to perform certain of the processes (e.g., the process 200) described herein using the processor 410 (e.g., one or more computer hardware processors) and one or more articles of manufacture that include non-transitory computer-readable storage media such as the memory 412. The processor 410 may control writing data to and reading data from the memory 412 in any suitable manner. To perform certain of the processes described herein, the processor 410 may execute one or more processor-executable instructions stored in one or more non-transitory computer-readable storage media (e.g., the memory 412), which may serve as non-transitory computer-readable storage media storing processor-executable instructions for execution by the processor 410. The camera 404 may be configured to detect light (e.g., visible light) to form an image. The camera 404 may be on the same face of the processing device 402 as the display screen 408. The display screen 408 may be configured to display images and/or videos, and may be, for example, a liquid crystal display (LCD), a plasma display, and/or an organic light emitting diode (OLED) display on the processing device 402. The input device 418 may include one or more devices capable of receiving input from a user and transmitting the input to the processor 410. For example, the input device 418 may include a keyboard, a mouse, a microphone, touch-enabled sensors on the display screen 408, and/or a microphone. The display screen 408, the input device 418, the camera 404, and the speaker 409 may be communicatively coupled to the processor 410 and/or under the control of the processor 410.

It should be appreciated that the processing device 402 may be implemented in any of a variety of ways. For example, the processing device 402 may be implemented as a handheld device such as a mobile smartphone or a tablet. Thereby, a user of the ultrasound device 406 may be able to operate the ultrasound device 406 with one hand and hold the processing device 402 with another hand. In other examples, the processing device 402 may be implemented as a portable device that is not a handheld device, such as a laptop. In yet other examples, the processing device 402 may be implemented as a stationary device such as a desktop computer. The processing device 402 may be connected to the network 416 over a wired connection (e.g., via an Ethernet cable) and/or a wireless connection (e.g., over a WiFi network). The processing device 402 may thereby communicate with (e.g., transmit data to) the one or more servers 434 over the network 416. For further description of ultrasound circuitry, devices, and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application), which is incorporated by reference herein in its entirety.

FIG. 4 should be understood to be non-limiting. For example, the ultrasound system 400, the ultrasound device 406, and/or the processing device 402 may include fewer or more components than shown.

Figure 5:
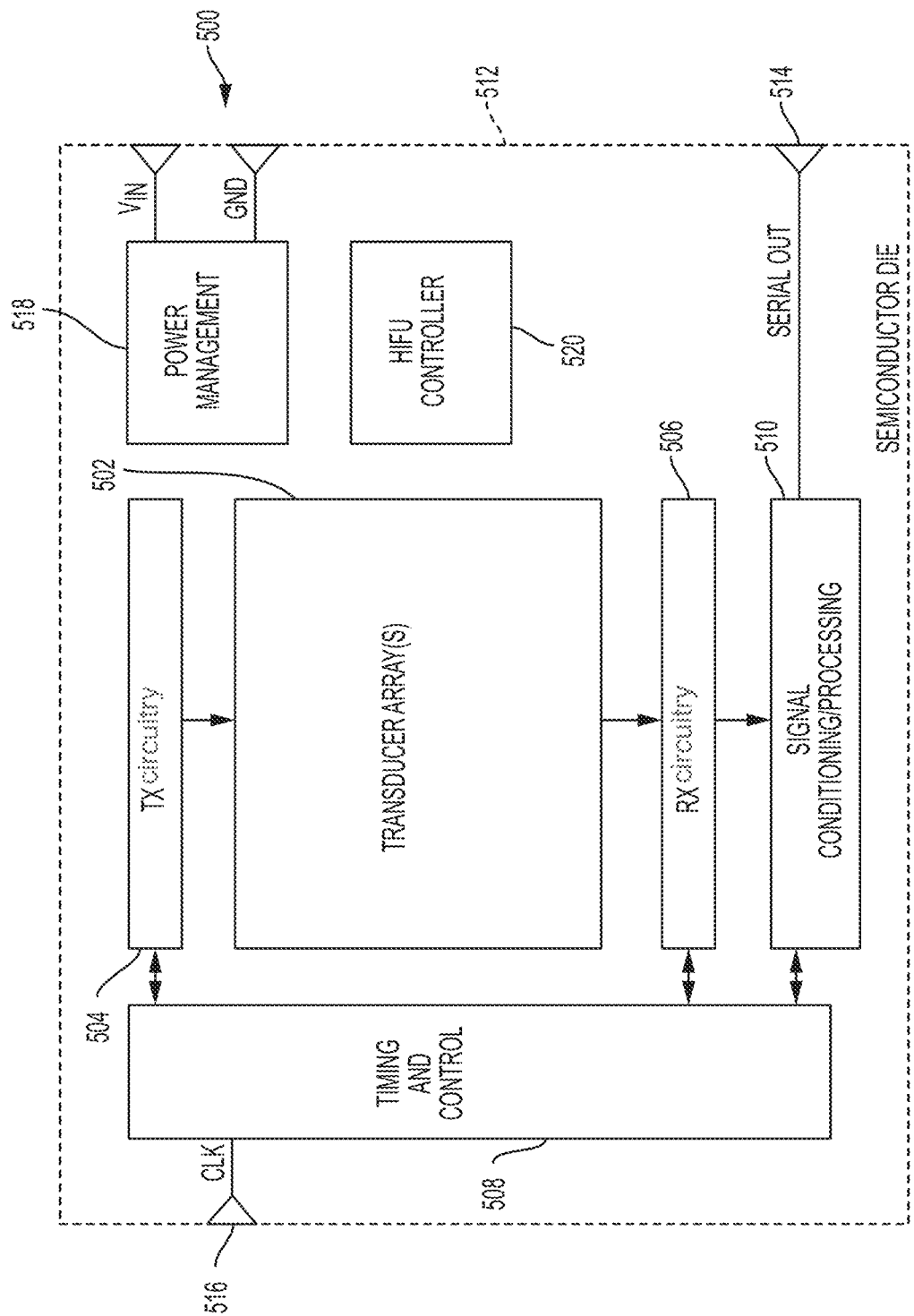
FIG. 5 illustrates a schematic block diagram of an example ultrasound device, in accordance with certain embodiments described herein.

FIG. 5 illustrates a schematic block diagram of an example ultrasound device 500, in accordance with certain embodiments described herein. As shown, the ultrasound device 500 includes one or more ultrasound transducer arrays 502, transmit (TX) circuitry 504, receive (RX) circuitry 506, a timing and control circuit 508, a signal conditioning/processing circuit 510, a power management circuit 518, and/or a high-intensity focused ultrasound (HIFU) controller 520. In the embodiment shown, all of the illustrated elements are integrated on a single semiconductor die 512. It should be appreciated, however, that in alternative embodiments one or more of the illustrated elements may be instead located off-die. It should be appreciated that communication between one or more of the illustrated components may be performed in any of numerous ways. In some embodiments, for example, one or more high-speed busses (not shown), such as that employed by a unified Northbridge, may be used to allow high-speed intra-die communication or communication with one or more off-die components.

The ultrasound device 500 may be the same as any of the ultrasound devices described herein (e.g., the ultrasound device that performs the process 100, the ultrasound device 500, the handheld ultrasound probe 700, the wearable ultrasound patch 800, and/or the ingestible ultrasound pill 900). The ultrasound transducer array 502 may be the same as the ultrasound transducers 411. Any combination of the TX circuitry 504, the RX circuitry 506, the timing and control circuit 508, the signal condition/processing circuit 510, the power management circuit 518, and the HIFU controller 520 may together constitute ultrasound circuitry that is the same as the ultrasound circuitry 409. The ultrasound device 500 may use the ultrasound transducer array 502 to transmit and/or receive ultrasound waves and may use some or all of the illustrated ultrasound circuitry to apply delays prior to transmission and/or subsequent to reception of the ultrasound waves in order to collect ultrasound data along different elevational steering angles with different apertures, as described with reference to the process 100.

The one or more ultrasound transducer arrays 502 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In some embodiments, the ultrasound transducer array 502 may be two-dimensional. In various embodiments, each of the transducer elements in the ultrasound transducer array 502 may, for example, include one or more capacitive micromachined ultrasound transducers (CMUTs), one or more CMOS ultrasound transducers (CUTs), one or more piezoelectric micromachined ultrasound transducers (PMUTs), and/or one or more other suitable ultrasound transducer cells.

A CUT may, for example, include a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasound transducer cell and integrated circuit on a single substrate (the CMOS wafer).

The TX circuitry 504 may, for example, generate pulses that drive the individual elements of, or one or more groups of elements within, the ultrasound transducer array(s) 502 so as to generate acoustic signals to be used for imaging. The RX circuitry 506, on the other hand, may receive and process electronic signals generated by the individual elements of the transducer array(s) 502 when acoustic signals impinge upon such elements.

In some embodiments, the timing and control circuit 508 may, for example, be responsible for generating all timing and control signals that are used to synchronize and coordinate the operation of the other elements in the ultrasound device 500. In the example shown, the timing and control circuit 508 is driven by a single clock signal CLK supplied to an input port 516. The clock signal CLK may, for example, be a high-frequency clock used to drive one or more of the on-die circuit components. In some embodiments, the clock signal CLK may, for example, be a 1.5625 GHz or 2.5 GHz clock used to drive a high-speed serial output device (not shown in FIG. 5) in the signal conditioning/processing circuit 510, or a 20 Mhz or 40 MHz clock used to drive other digital components on the semiconductor die 512, and the timing and control circuit 508 may divide or multiply the clock CLK, as necessary, to drive other components on the die 512. In other embodiments, two or more clocks of different frequencies (such as those referenced above) may be separately supplied to the timing and control circuit 508 from an off-die source.

The power management circuit 518 may, for example, be responsible for converting one or more input voltages VIN from an off-die source into voltages needed to carry out operation of the die, and for otherwise managing power consumption within the ultrasound device 500. In some embodiments, for example, a single voltage (e.g., 12V, 80V, 100V, 120V, etc.) may be supplied to the die and the power management circuit 518 may step that voltage up or down, as necessary, using a charge pump circuit or via some other DC-to-DC voltage conversion mechanism. In other embodiments, multiple different voltages may be supplied separately to the power management circuit 518 for processing and/or distribution to the other on-die components.

As shown in FIG. 5, in some embodiments, a HIFU controller 520 may be integrated on the semiconductor die 512 so as to enable the generation of HIFU signals via one or more elements of the ultrasound transducer array(s) 502. In other embodiments, a HIFU controller for driving the ultrasound transducer array(s) 502 may be located off-die. That is, aspects of the present disclosure relate to provision of ultrasound-on-a-die HIFU systems, with and without ultrasound imaging capability. It should be appreciated, however, that some embodiments may not have any HIFU capabilities and thus may not include a HIFU controller 520.

Moreover, it should be appreciated that the HIFU controller 520 may not represent distinct circuitry in those embodiments providing HIFU functionality. For example, in some embodiments, the remaining circuitry of FIG. 5 (other than the HIFU controller 520) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-die control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-die circuitry may be utilized to provide both functions, with suitable timing sequences used to control the operation between the two modalities.

In the example shown, one or more output ports 514 may output a high-speed serial data stream generated by one or more components of the signal conditioning/processing circuit 510. Such data streams may, for example, be generated by one or more USB 3.0 modules, and/or one or more 10 GB, 40 GB, or 100 GB Ethernet modules, integrated on the semiconductor die 512. In some embodiments, the signal stream produced on output port 514 can be fed to a computer, tablet, or smartphone for the generation and/or display of 2-dimensional, 3-dimensional, and/or tomographic images. In embodiments in which image formation capabilities are incorporated in the signal conditioning/processing circuit 510, even relatively low-power devices, such as smartphones or tablets which have only a limited amount of processing power and memory available for application execution, can display images using only a serial data stream from the output port 514. As noted above, the use of on-die analog-to-digital conversion and a high-speed serial data link to offload a digital data stream is one of the features that helps facilitate an "ultrasound on a die" solution according to some embodiments of the technology described herein.

Ultrasound devices 500 such as that shown in FIG. 5 may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's bladder, by energizing some or all of the elements in the ultrasound transducer array(s) 502 (either together or individually) during one or more transmit phases, and receiving and processing signals generated by some or all of the elements in the ultrasound transducer array(s) 502 during one or more receive phases, such that during each receive phase the CMUT elements sense acoustic signals reflected by the subject. In other implementations, some of the elements in the ultrasound transducer array(s) 502 may be used only to transmit acoustic signals and other elements in the same ultrasound transducer array(s) 502 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUTs.

Figure 6:
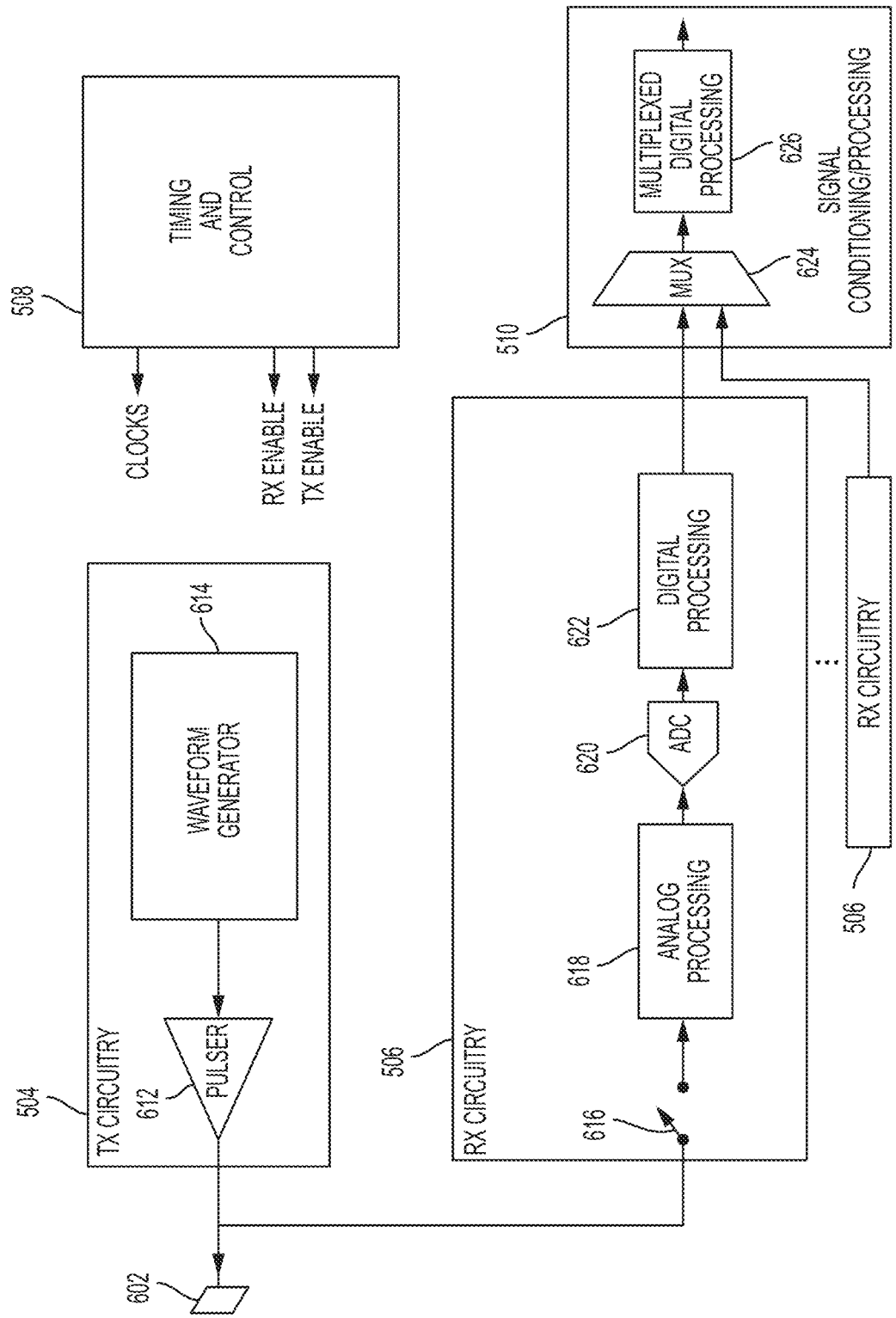
FIG. 6 illustrates another schematic block diagram of the example ultrasound device of FIG. 5, in accordance with certain embodiments described herein.

FIG. 6 illustrates another schematic block diagram of the example ultrasound device 500, in accordance with certain embodiments described herein. In particular, FIG. 6 illustrates how, in some embodiments, the TX circuitry 504 and the RX circuitry 506 for a given transducer element 602 of the ultrasound transducer array 502 may be used either to energize the transducer element 602 to emit an ultrasonic pulse, or to receive and process a signal from the transducer element 602 representing an ultrasonic pulse sensed by it. In some implementations, the TX circuitry 504 may be used during a "transmission" phase, and the RX circuitry may be used during a "reception" phase that is non-overlapping with the transmission phase. In other implementations, one of the TX circuitry 504 and the RX circuitry 506 may simply not be used, such as when a pair of ultrasound units is used for only transmissive imaging. As noted above, in some embodiments, the ultrasound device 500 may alternatively employ only TX circuitry 504 or only RX circuitry 506, and aspects of the present technology do not necessarily require the presence of both such types of circuitry. In various embodiments, TX circuitry 504 and/or RX circuitry 506 may include a TX circuit and/or an RX circuit associated with a single transducer cell (e.g., a CUT or CMUT), a group of two or more transducer cells within a single transducer element 602, a single transducer element 602 comprising a group of transducer cells, a group of two or more transducer elements 602 within an ultrasound transducer array 502, or an entire ultrasound transducer array 502 of transducer elements 602.

In the example shown in FIG. 6, the TX circuitry 504/RX circuitry 506 includes a separate TX circuit and a separate RX circuit for each transducer element 602 in the ultrasound transducer array(s) 502, but there is only one instance of each of the timing & control circuit 508 and the signal conditioning/processing circuit 510. Accordingly, in such an implementation, the timing & control circuit 508 may be responsible for synchronizing and coordinating the operation of all of the TX circuitry 504/RX circuitry 506 combinations on the die 512, and the signal conditioning/processing circuit 510 may be responsible for handling inputs from all of the RX circuitry 506 on the die 512. In other embodiments, timing and control circuit 508 may be replicated for each transducer element 602 or for a group of transducer elements 602.

As shown in FIG. 6, in addition to generating and/or distributing clock signals to drive the various digital components in the ultrasound device 500, the timing & control circuit 508 may output either an "TX enable" signal to enable the operation of each TX circuit of the TX circuitry 504, or an "RX enable" signal to enable operation of each RX circuit of the RX circuitry 506. In the example shown, a switch 616 in the RX circuitry 506 may always be opened before the TX circuitry 504 is enabled, so as to prevent an output of the TX circuitry 504 from driving the RX circuitry 506. The switch 616 may be closed when operation of the RX circuitry 506 is enabled, so as to allow the RX circuitry 506 to receive and process a signal generated by the transducer element 602.

As shown, the TX circuitry 504 for a respective transducer element 602 may include both a waveform generator 614 and a pulser 612. The waveform generator 614 may, for example, be responsible for generating a waveform that is to be applied to the pulser 612, so as to cause the pulser 612 to output a driving signal to the transducer element 602 corresponding to the generated waveform.

In the example shown in FIG. 6, the RX circuitry 506 for a respective transducer element 602 includes an analog processing block 618, an analog-to-digital converter (ADC) 620, and a digital processing block 622. The ADC 620 may, for example, comprise a 10-bit or 12-bit, 20 Msps, 25 Msps, 40 Msps, 50 Msps, or 80 Msps ADC.

After undergoing processing in the digital processing block 622, the outputs of all of the RX circuits on the semiconductor die 512 (the number of which, in this example, is equal to the number of transducer elements 602 on the die) are fed to a multiplexer (MUX) 624 in the signal conditioning/processing circuit 510. In other embodiments, the number of transducer elements is larger than the number of RX circuits, and several transducer elements provide signals to a single RX circuit. The MUX 624 multiplexes the digital data from the RX circuits, and the output of the MUX 624 is fed to a multiplexed digital processing block 626 in the signal conditioning/processing circuit 510, for final processing before the data is output from the semiconductor die 512, e.g., via one or more high-speed serial output ports 514. The MUX 624 is optional, and in some embodiments parallel signal processing is performed. A high-speed serial data port may be provided at any interface between or within blocks, any interface between dies and/or any interface to a host. Various components in the analog processing block 618 and/or the digital processing block 622 may reduce the amount of data that needs to be output from the semiconductor die 512 via a high-speed serial data link or otherwise. In some embodiments, for example, one or more components in the analog processing block 618 and/or the digital processing block 622 may thus serve to allow the RX circuitry 506 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-die" solution in some embodiments.

Figure 7:
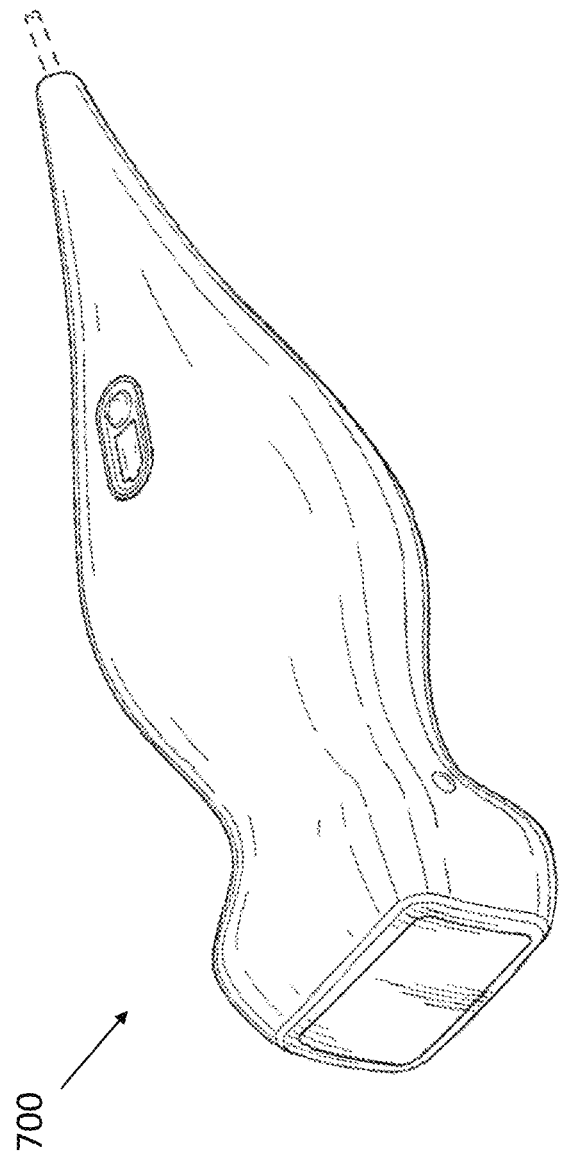
FIG. 7 illustrates an example handheld ultrasound probe, in accordance with certain embodiments described herein.

FIG. 7 illustrates an example handheld ultrasound probe 700, in accordance with certain embodiments described herein. The handheld ultrasound probe 700 may be the same as the ultrasound device that performs the process 100, ultrasound device 406, and/or the ultrasound device 500 and may contain ultrasound transducers (e.g., the ultrasound transducers 411 and/or the ultrasound transducer array 502) and any or all of the ultrasound circuitry illustrated in FIGS. 4-6 (e.g., the transmit (TX) circuitry 504, the receive (RX) circuitry 506, the timing and control circuit 508, the signal conditioning/processing circuit 510, the power management circuit 518, the high-intensity focused ultrasound (HIFU) controller 520, the waveform generator 614, the pulser 612, the switch 616, the analog processing block 618, the ADC 620, the digital processing block 622, the multiplexer 624, and the multiplexed digital processing block 626. The ultrasound transducers and some or all of the ultrasound circuitry may be integrated on a die (e.g., the die 512) that is contained in the handheld ultrasound probe.

Figure 8:
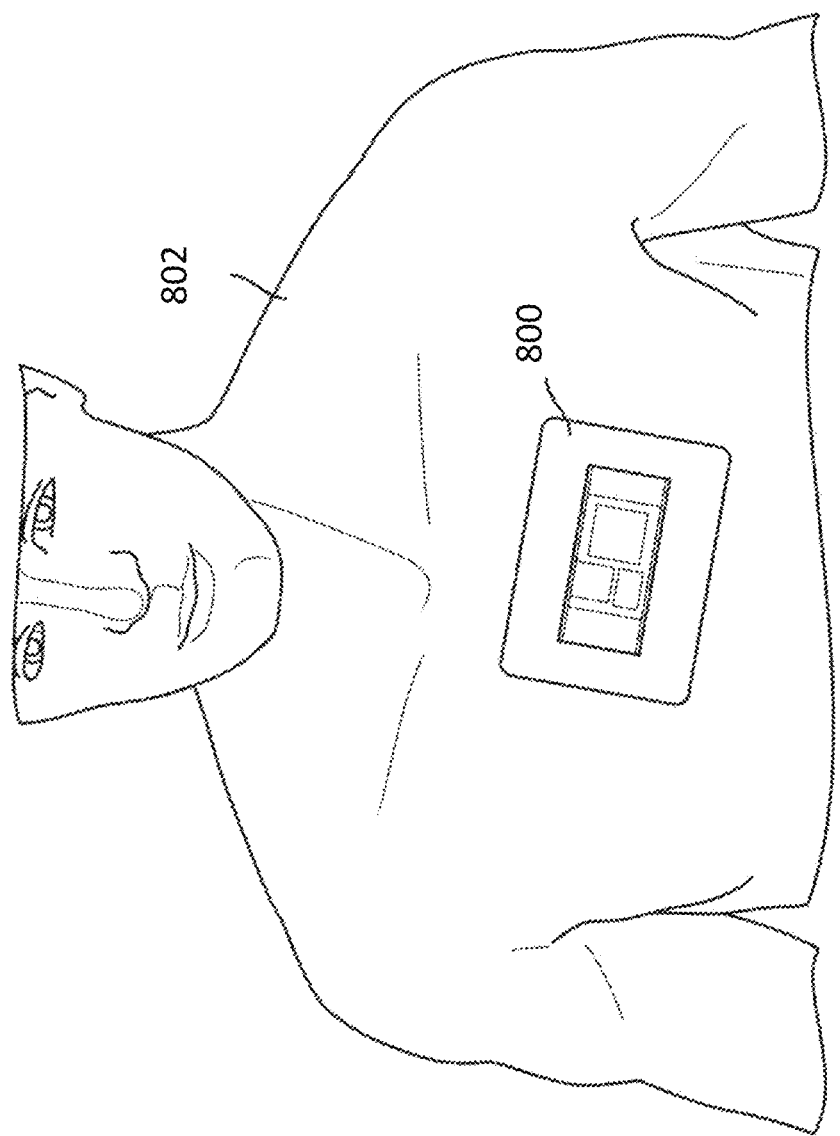
FIG. 8 illustrates an example wearable ultrasound patch, in accordance with certain embodiments described herein.

FIG. 8 illustrates an example wearable ultrasound patch 800, in accordance with certain embodiments described herein. The wearable ultrasound patch 800 is coupled to a subject 802. The wearable ultrasound patch 800 may be the same as the ultrasound device that performs the process 100, the ultrasound device 406, and/or the ultrasound device 500 and may contain ultrasound transducers (e.g., the ultrasound transducers 411 and/or the ultrasound transducer array 502) and any or all of the ultrasound circuitry illustrated in FIGS. 4-6 (e.g., the transmit (TX) circuitry 504, the receive (RX) circuitry 506, the timing and control circuit 508, the signal conditioning/processing circuit 510, the power management circuit 518, the high-intensity focused ultrasound (HIFU) controller 520, the waveform generator 614, the pulser 612, the switch 616, the analog processing block 618, the ADC 620, the digital processing block 622, the multiplexer 624, and the multiplexed digital processing block 626. The ultrasound transducers and some or all of the ultrasound circuitry may be integrated on a die (e.g., the die 512) that is contained in the handheld ultrasound probe.

Figure 9:
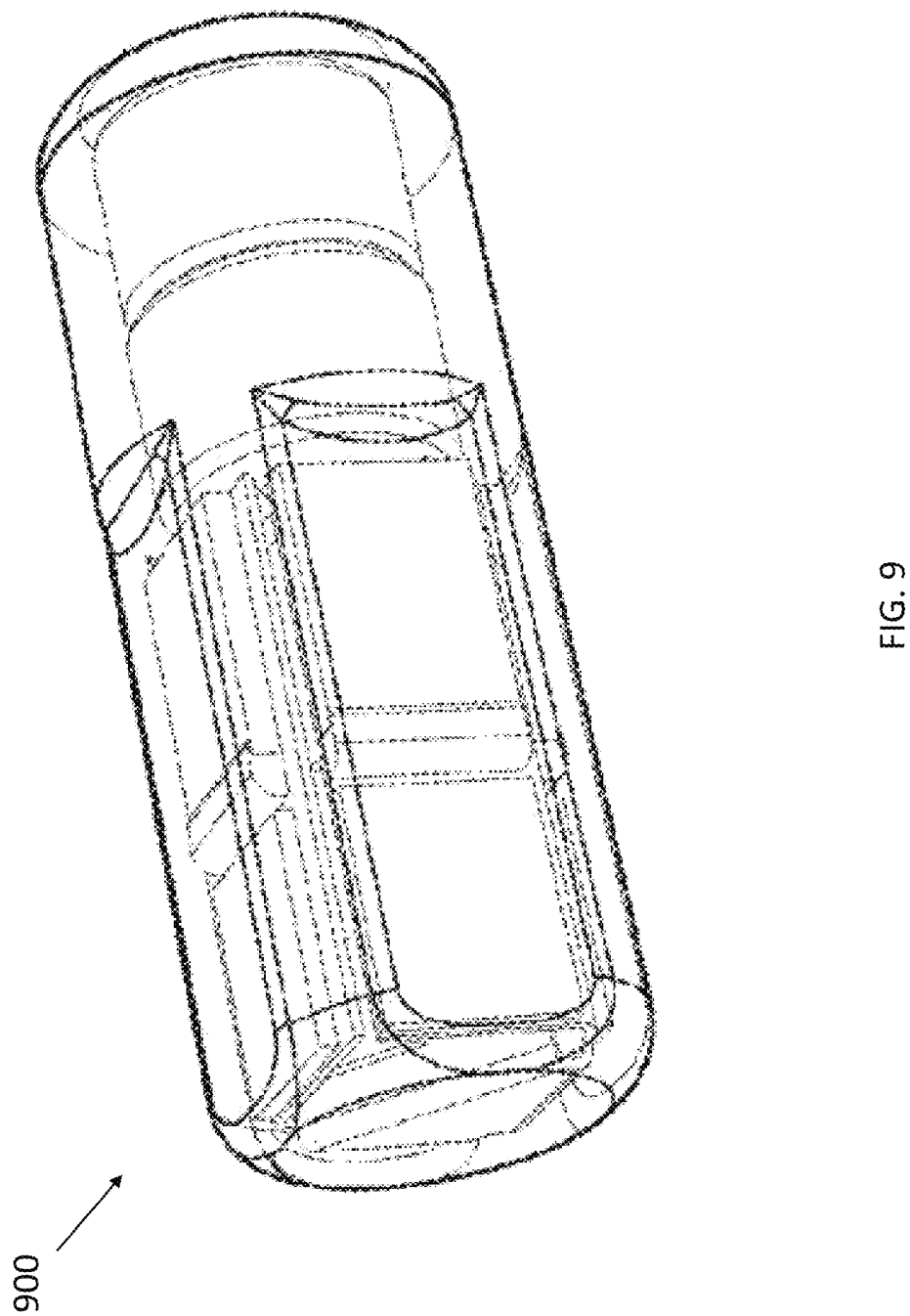
FIG. 9 illustrates an example ingestible ultrasound pill, in accordance with certain embodiments described herein.

FIG. 9 illustrates an example ingestible ultrasound pill 900, in accordance with certain embodiments described herein. The ingestible ultrasound pill 900 may be the same as the ultrasound device that performs the process 100, the ultrasound device 406, and/or the ultrasound device 500 and may contain ultrasound transducers (e.g., the ultrasound transducers 411 and/or the ultrasound transducer array 502) and any or all of the ultrasound circuitry illustrated in FIGS. 4-6 (e.g., the transmit (TX) circuitry 504, the receive (RX) circuitry 506, the timing and control circuit 508, the signal conditioning/processing circuit 510, the power management circuit 518, the high-intensity focused ultrasound (HIFU) controller 520, the waveform generator 614, the pulser 612, the switch 616, the analog processing block 618, the ADC 620, the digital processing block 622, the multiplexer 624, and the multiplexed digital processing block 626. The ultrasound transducers and some or all of the ultrasound circuitry may be integrated on a die (e.g., the die 512) that is contained in the handheld ultrasound probe.

Further description of the handheld ultrasound probe 700, the wearable ultrasound patch 800, and the ingestible ultrasound pill 900 may be found in U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application).

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Various inventive concepts may be embodied as one or more processes, of which an example has been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device, the ultrasound device comprising:
   an ultrasound transducer array,
   wherein:
      the ultrasound device is configured to:
         collect first ultrasound data using ultrasound waves focused along a first elevational steering angle with a first aperture of the ultrasound transducer array; and
         collect second ultrasound data using ultrasound waves focused along a second elevational steering angle with a second aperture of the ultrasound transducer array, wherein the first elevational steering angle deviates more from a normal to an elevational dimension of the ultrasound transducer array than the second elevational steering angle;
      the first aperture is a different size than the second aperture; and
      the first aperture comprises a first number of elevational rows of the ultrasound transducer array, the second aperture comprises a second number of elevational rows of the ultrasound transducer array, and the first number is greater than the second number.

2. The ultrasound device of claim 1, wherein the first number of elevational rows and the second number of elevational rows are between 8-64.

3. The ultrasound device of claim 1, wherein the first and second elevational steering angles are among a plurality of elevational steering angles used in an ultrasound imaging sweep, and wherein the plurality of elevational steering angles includes between 30-50 steering angles.

4. The ultrasound device of claim 1, wherein the first and second elevational steering angles are among a plurality of elevational steering angles that are varied with respect to an axis that is parallel to a skin line of a subject being imaged.

5. The ultrasound device of claim 1, wherein the ultrasound device further comprises ultrasound circuitry, and the ultrasound device is configured, when collecting the first and second ultrasound data, to use the ultrasound circuitry to apply delays to the ultrasound waves at a point in time selected from a group consisting of:

prior to transmission, and subsequent to reception.

6. The ultrasound device of claim 5, wherein the ultrasound circuitry is integrated on a same die as the ultrasound transducer array.

7. The ultrasound device of claim 5, wherein the ultrasound circuitry includes at least one of a waveform generator, a pulser, an analog processing block, an analog-to-digital converter, and a digital processing block.

8. The ultrasound device of claim 5, wherein the ultrasound device is portable and the ultrasound transducer array and the ultrasound circuitry are contained within the portable ultrasound device.

9. The ultrasound device of claim 5, wherein the ultrasound device is a handheld probe and the ultrasound transducer array and the ultrasound circuitry are contained within the handheld probe.

10. The ultrasound device of claim 5, wherein the ultrasound device is a wearable patch and the ultrasound transducer array and the ultrasound circuitry are contained within the wearable patch.

11. The ultrasound device of claim 1, wherein the ultrasound device is configured to operatively communicate with a processing device, and the ultrasound device is further configured to transmit at least one selected from a group consisting of:

the first and second ultrasound data, and data generated based on the first and second ultrasound data to the processing device.

12. The ultrasound device of claim 11, wherein the processing device is a smartphone, tablet, or laptop.

13. An ultrasound device, the ultrasound device comprising:

an ultrasound transducer array, wherein:

the ultrasound device is configured to:

collect first ultrasound data using ultrasound waves focused along a first elevational steering angle with a first aperture of the ultrasound transducer array; and collect second ultrasound data using ultrasound waves focused along a second elevational steering angle with a second aperture of the ultrasound transducer array;

the first aperture is a different size than the second aperture; and the first elevational steering angle deviates more from a normal to an elevational dimension of the ultrasound transducer array than the second elevational steering angle, and the first aperture is larger than the second aperture.

14. The ultrasound device of claim 13, wherein the ultrasound device is configured to collect the first ultrasound data and the second ultrasound data as part of a single scan.

15. The ultrasound device of claim 13, wherein the ultrasound device is configured to collect the first ultrasound data and the second ultrasound data as part of a single ultrasound imaging sweep.

16. The ultrasound device of claim 15, wherein the ultrasound imaging sweep comprises an elevational sweep.

17. The ultrasound device of claim 13, wherein the ultrasound device is further configured to digitally beamform the first and second ultrasound data along an elevational dimension of the ultrasound transducer array.

18. The ultrasound device of claim 13, wherein the ultrasound device is configured, when collecting the first and second ultrasound data, to collect ultrasound data from a bladder.

19. The ultrasound device of claim 13, wherein the first and second elevational steering angles are among a plurality of elevational steering angles used in an ultrasound 1magmg sweep, and wherein the plurality of elevational steering angles includes between 30-50 steering angles.

20. The ultrasound device of claim 13, wherein the first and second elevational steering angles are among a plurality of elevational steering angles that are varied with respect to an axis that is parallel to a skin line of a subject being imaged.

* * * * *